United States Patent
Honda

(10) Patent No.: US 9,662,097 B2
(45) Date of Patent: May 30, 2017

(54) METHOD FOR RETRIEVING OBJECTS FROM A LIVING BODY AND EXPANDING A NARROWED REGION IN THE LIVING BODY

(71) Applicant: TERUMO KABUSHIKI KAISHA, Tokyo (JP)

(72) Inventor: Kei Honda, Hadano (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 120 days.

(21) Appl. No.: 14/675,718

(22) Filed: Mar. 31, 2015

(65) Prior Publication Data

US 2016/0287275 A1    Oct. 6, 2016

(51) Int. Cl.
*A61B 17/22*    (2006.01)
*A61B 17/00*    (2006.01)

(52) U.S. Cl.
CPC ........ *A61B 17/00234* (2013.01); *A61B 17/22* (2013.01); *A61B 2017/22079* (2013.01); *A61B 2017/22084* (2013.01)

(58) Field of Classification Search
CPC .................. A61B 17/22; A61B 17/221; A61B 2017/00292; A61B 2017/00296; A61B 2017/0034; A61B 2017/22038; A61B 2017/22042; A61B 2017/22072; A61B 2017/22074; A61B 2017/22075; A61B 2017/22078; A61B 2017/22079; A61B 2017/22081; A61B 2017/22094; A61B 2017/2215; A61B 2017/2217

See application file for complete search history.

(56) References Cited

U.S. PATENT DOCUMENTS

| | | | | |
|---|---|---|---|---|
| 4,696,297 A | * | 9/1987 | Pleines | A61B 17/22 606/22 |
| 4,784,636 A | * | 11/1988 | Rydell | A61B 17/320758 600/568 |
| 4,926,858 A | * | 5/1990 | Gifford, III | A61B 17/22031 604/22 |
| 5,085,662 A | * | 2/1992 | Willard | A61B 17/22012 606/159 |
| 5,423,838 A | * | 6/1995 | Willard | A61B 17/22012 600/439 |
| 5,989,266 A | * | 11/1999 | Foster | A61B 17/221 606/114 |
| 6,174,307 B1 | * | 1/2001 | Daniel | A61B 1/00098 600/103 |

(Continued)

OTHER PUBLICATIONS

U.S. Appl. No. 14/222,021, filed Mar. 21, 2014, Kei Honda.
U.S. Appl. No. 14/221,954, filed Mar. 21, 2014, Kei Honda.
U.S. Appl. No. 14/221,858, filed Mar. 21, 2014, Kei Honda.

*Primary Examiner* — Ryan J Severson
(74) *Attorney, Agent, or Firm* — Buchanan Ingersoll & Rooney PC

(57) ABSTRACT

A method of expanding a narrowed region inside a living body involves positioning a liquid introducer in the narrowed region in the living body and introducing liquid into the narrowed region by way of the liquid introducer. The liquid applies an outwardly directed force on the narrowed region to expand the narrowed region. The narrowed region includes the renal pelvis, the entrance to the lower calix, the ureter, etc.

20 Claims, 9 Drawing Sheets

(56) References Cited

U.S. PATENT DOCUMENTS

| | | | | |
|---|---|---|---|---|
| 6,238,401 B1* | 5/2001 | Richter | A61B 1/00147 | 128/898 |
| 6,258,083 B1* | 7/2001 | Daniel | A61B 1/00098 | 606/15 |
| 6,544,227 B2* | 4/2003 | Sahatjian | A61B 17/22012 | 604/113 |
| 6,565,530 B2* | 5/2003 | Sahatjian | A61B 17/22012 | 604/113 |
| 6,663,594 B2* | 12/2003 | Sahatjian | A61B 17/22012 | 604/113 |
| 6,692,484 B1* | 2/2004 | Karpiel | A61B 17/22031 | 600/31 |
| 6,866,651 B2* | 3/2005 | Constantz | A61B 17/22 | 514/891 |
| 7,101,379 B2* | 9/2006 | Gregory, Jr. | A61B 17/221 | 606/127 |
| 7,137,966 B2* | 11/2006 | Sahatjian | A61B 17/22012 | 604/113 |
| RE40,305 E * | 5/2008 | Richter | A61B 1/00147 | 128/898 |
| 7,582,054 B2* | 9/2009 | Okada | A61B 1/00133 | 600/104 |
| 7,731,722 B2* | 6/2010 | Lavelle | A61B 17/221 | 606/127 |
| 7,837,672 B2* | 11/2010 | Intoccia | A61B 17/22 | 604/101.01 |
| 7,906,152 B2* | 3/2011 | Constantz | A61B 17/22 | 424/666 |
| 7,946,978 B2* | 5/2011 | Okada | A61B 1/00133 | 600/104 |
| 7,963,944 B2* | 6/2011 | Sahatjian | A61B 17/22012 | 604/113 |
| 8,197,463 B2* | 6/2012 | Intoccia | A61B 17/22 | 604/101.01 |
| 8,372,037 B2* | 2/2013 | Sahatjian | A61B 17/22012 | 604/113 |
| 8,394,059 B2* | 3/2013 | Sahatjian | A61B 17/22012 | 604/113 |
| 8,409,218 B2* | 4/2013 | Schwarz | A61B 17/12022 | 600/420 |
| 8,409,237 B2* | 4/2013 | Galdonik | A61B 17/22 | 606/200 |
| 8,679,059 B2* | 3/2014 | Sahatjian | A61B 17/22012 | 604/113 |
| 8,834,416 B2* | 9/2014 | Sahatjian | A61B 17/22012 | 604/113 |
| 8,998,928 B2* | 4/2015 | Schwarz | A61B 17/12022 | 600/430 |
| 2001/0025174 A1* | 9/2001 | Daniel | A61B 1/00098 | 606/15 |
| 2002/0119116 A1* | 8/2002 | Sahatjian | A61B 17/22012 | 424/78.31 |
| 2002/0120237 A1* | 8/2002 | Sahatjian | A61B 17/22012 | 604/180 |
| 2003/0088254 A1* | 5/2003 | Gregory, Jr. | A61B 17/221 | 606/127 |
| 2003/0178030 A1* | 9/2003 | Constantz | A61B 17/22 | 128/898 |
| 2003/0195464 A1* | 10/2003 | Sahatjian | A61B 17/22012 | 604/113 |
| 2003/0229332 A1* | 12/2003 | Intoccia | A61B 17/22 | 604/508 |
| 2004/0019358 A1* | 1/2004 | Kear | A61B 17/22031 | 606/127 |
| 2005/0043756 A1* | 2/2005 | Lavelle | A61B 17/221 | 606/200 |
| 2005/0053662 A1* | 3/2005 | Sahatjian | A61B 17/22012 | 424/486 |
| 2005/0119522 A1* | 6/2005 | Okada | A61B 1/00133 | 600/106 |
| 2005/0143678 A1* | 6/2005 | Schwarz | A61B 17/12022 | 601/4 |
| 2005/0251104 A1* | 11/2005 | Constantz | A61B 17/22 | 604/514 |
| 2005/0277976 A1* | 12/2005 | Galdonik | A61B 17/22 | 606/200 |
| 2006/0189921 A1* | 8/2006 | Galdonik | A61B 17/22 | 604/27 |
| 2006/0233891 A1* | 10/2006 | Constantz | A61B 17/22 | 424/666 |
| 2007/0066933 A1* | 3/2007 | Sahatjian | A61B 17/22012 | 604/23 |
| 2007/0088256 A1* | 4/2007 | Intoccia | A61B 17/22 | 604/102.02 |
| 2008/0015410 A1* | 1/2008 | Okada | A61B 1/00133 | 600/107 |
| 2008/0103481 A1* | 5/2008 | Vogel | A61B 17/12022 | 604/514 |
| 2008/0188866 A1* | 8/2008 | Karpiel | A61B 17/22032 | 606/127 |
| 2010/0274231 A1* | 10/2010 | Pravong | A61B 17/22 | 606/2.5 |
| 2011/0060256 A1* | 3/2011 | Schwarz | A61B 17/12022 | 601/4 |
| 2011/0092957 A1* | 4/2011 | Intoccia | A61B 17/22 | 604/540 |
| 2011/0245801 A1* | 10/2011 | Sahatjian | A61B 17/22012 | 604/506 |
| 2012/0010595 A1* | 1/2012 | Sahatjian | A61B 17/22012 | 604/506 |
| 2013/0131445 A1* | 5/2013 | Zerfas | A61B 17/22 | 600/104 |
| 2013/0150789 A1* | 6/2013 | Sahatjian | A61B 17/22012 | 604/131 |
| 2013/0172789 A1* | 7/2013 | Schwarz | A61B 17/12022 | 601/4 |
| 2013/0231676 A1* | 9/2013 | Sahatjian | A61B 17/22012 | 606/127 |
| 2015/0265294 A1* | 9/2015 | Honda | A61B 17/22 | 606/128 |
| 2015/0265295 A1* | 9/2015 | Honda | A61B 17/22 | 606/127 |
| 2015/0265296 A1* | 9/2015 | Honda | A61B 17/22 | 606/127 |
| 2015/0265297 A1* | 9/2015 | Honda | A61B 17/22 | 606/127 |
| 2015/0265298 A1* | 9/2015 | Honda | A61B 17/22 | 606/127 |
| 2016/0015393 A1* | 1/2016 | Schwarz | A61B 17/12022 | 601/4 |
| 2016/0081701 A1* | 3/2016 | Honda | A61B 17/221 | 606/127 |
| 2016/0081703 A1* | 3/2016 | Honda | A61B 17/22031 | 606/127 |
| 2016/0089171 A1* | 3/2016 | Honda | A61B 17/22 | 606/128 |
| 2016/0089173 A1* | 3/2016 | Honda | A61B 17/22031 | 606/127 |
| 2016/0089174 A1* | 3/2016 | Honda | A61B 17/22031 | 606/127 |
| 2016/0089185 A1* | 3/2016 | Honda | A61B 17/50 | 606/127 |

* cited by examiner

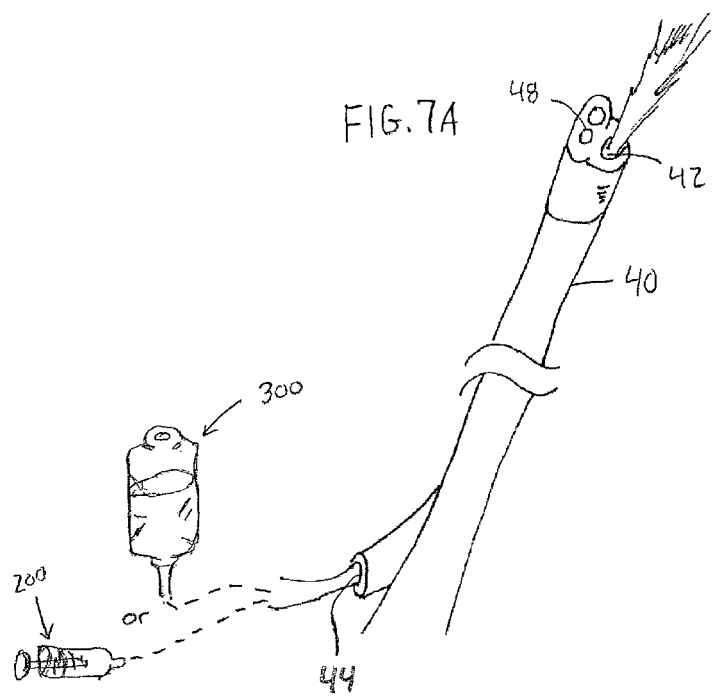
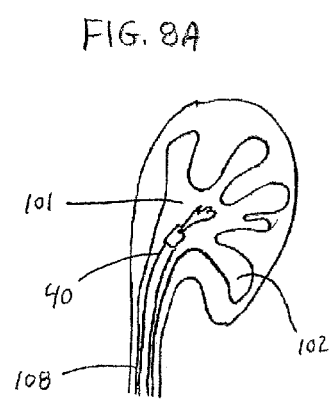
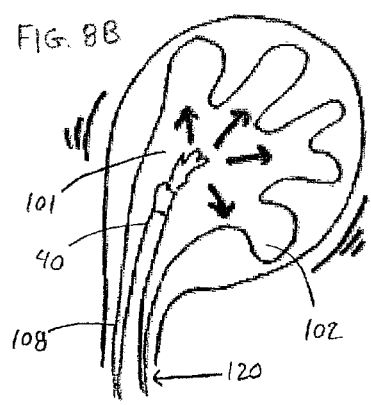

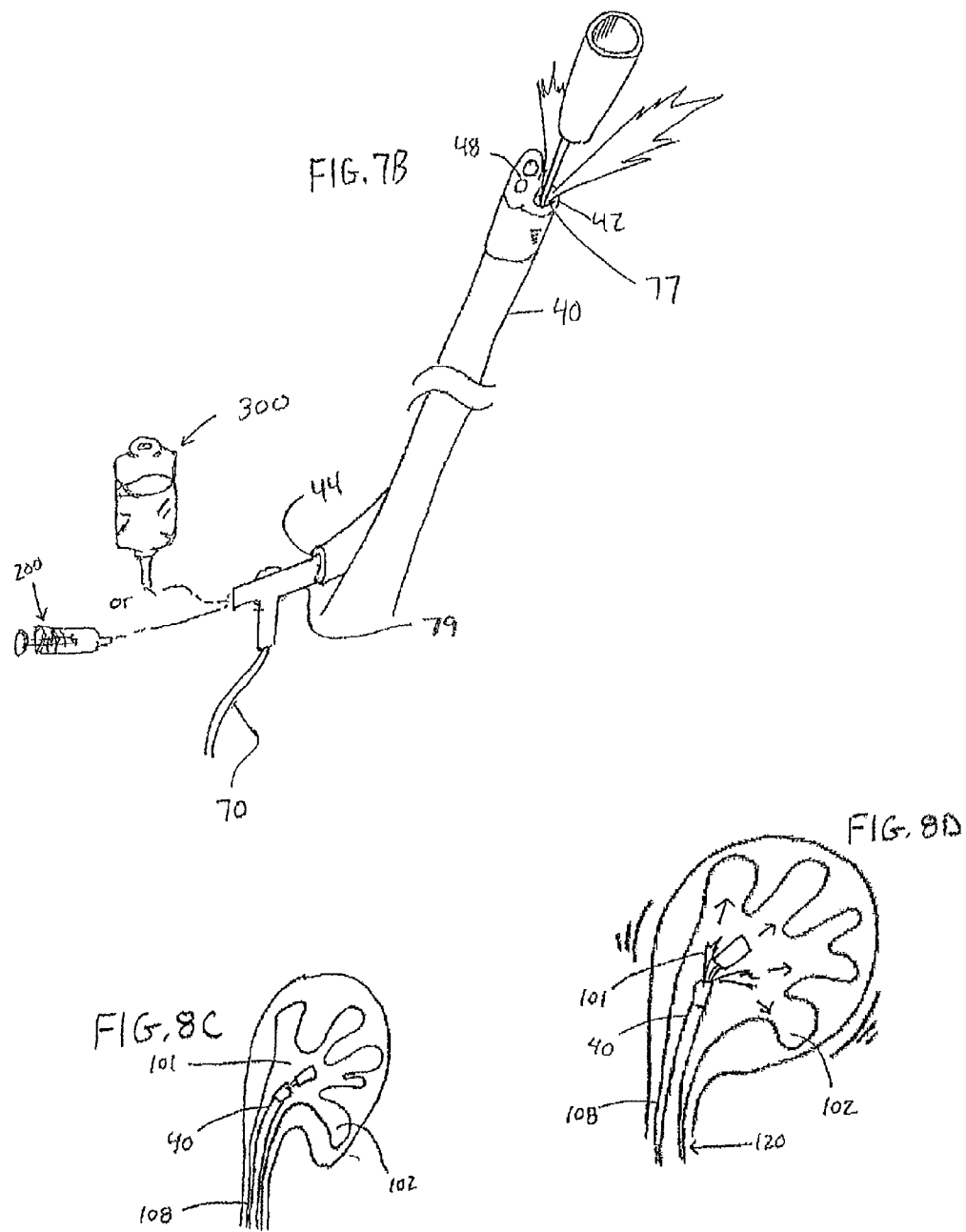

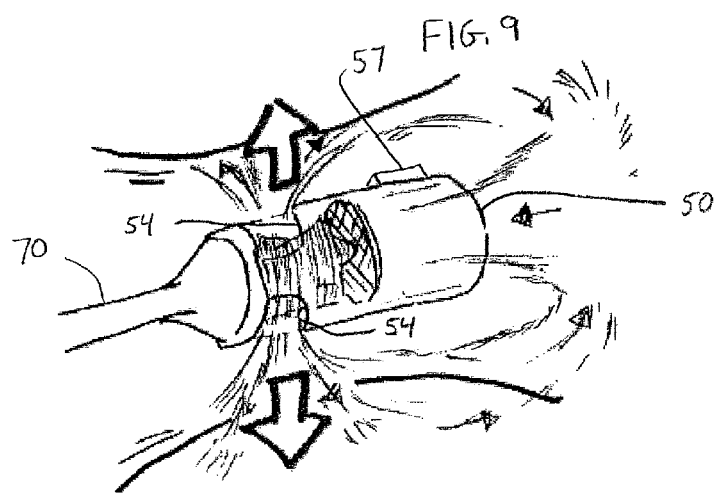
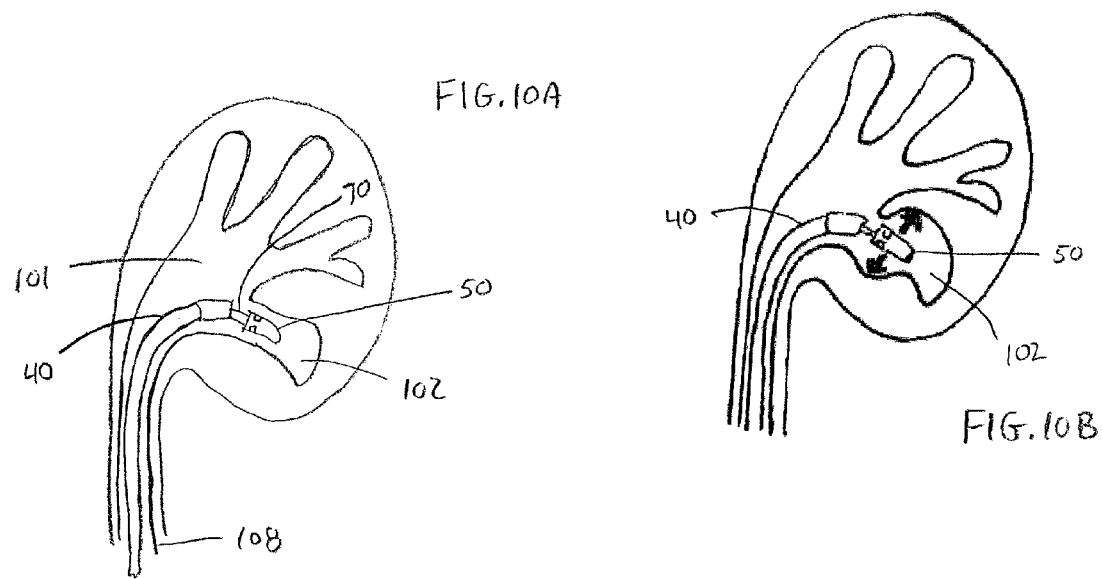

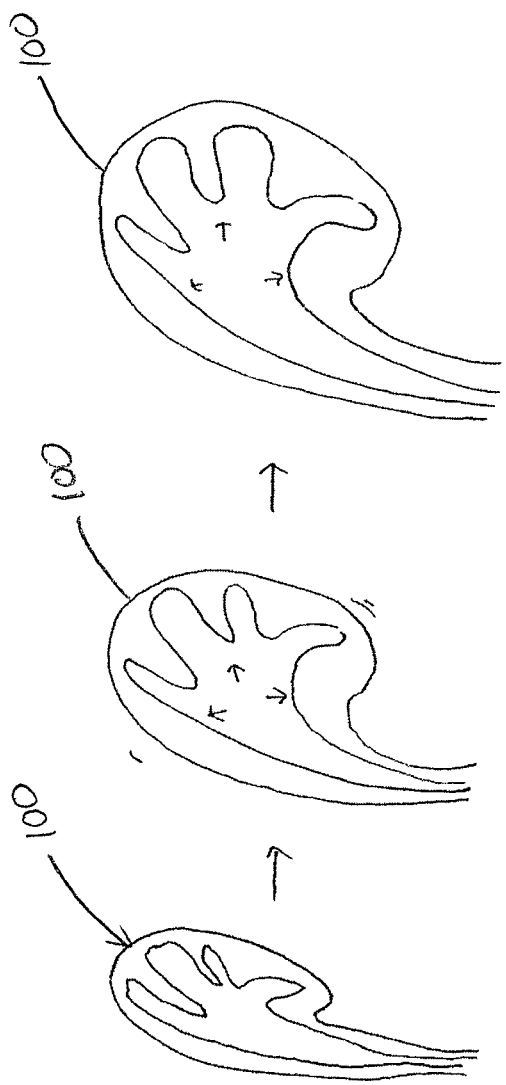

METHOD FOR RETRIEVING OBJECTS FROM A LIVING BODY AND EXPANDING A NARROWED REGION IN THE LIVING BODY

CROSS-REFERENCE TO OTHER APPLICATIONS

This application discloses subject matter related to subject matter described in U.S. application Ser. No. 14/222,021, U.S. application Ser. No. 14/221,954 and U.S. application Ser. No. 14/221,858, the entire content of each of which is incorporated herein by reference.

TECHNICAL FIELD

The present invention generally pertains to methods and systems for retrieving/removing a mass from a human body, and methods for increasing the size of a narrowed region in the living body. More specifically, the invention involves methods and systems for retrieving/removing stone(s) (e.g., calculus or calculi) from a portion of a human body such as the renal pelvis or the ureter, as well as methods for expanding narrow regions in the living body such as the renal pelvis, the entrance to the lower calix, etc.

BACKGROUND DISCUSSION

The term urinary calculus (calculi) (e.g., kidney stone(s) and ureteral stone(s)) refers to mass(es) or stone(s), typically solid particle(s), that form in the human body and is located in the kidney and/or the ureter. They can exhibit a variety of chemical compositions including calcium oxalate, calcium phosphate, uric acid, cystine, and struvite.

Stone disease (e.g., kidney stones and ureteral stones) is a relatively common urological disorder. The presence of calculus in the body can manifest itself in a variety of ways and can produce a number of medical ailments. For example, the presence of calculus in the renal pelvis and/or the renal calix (i.e., the lumen of the kidney) can cause blood in the urine, urinary obstruction, infection, and various degrees of pain ranging from vague frank pain to much more severe pain not capable of being relieved through general pain medication. The presence of stones or calculi in the ureter can result in relatively severe side and back pain, pain below the ribs, and pain that sometimes spread to the lower abdomen and groin, as well as pain during urination and hematuria.

Fortunately, many calculi or stones pass out of the body without requiring any specific medical intervention. In those situations where the calculus does not naturally pass out of the body, a medical procedure may be required. Known medical procedures typically fall into three categories.

In the past, three main treatments have been used to address calculus or kidney stones. These include shock wave lithotripsy (ESWL), transurethral lithotripsy or ureteroscopy (URS), and percutaneous nephrouretero lithotripsy (PCNL) which is sometimes also referred to as percutaneous nephrolithotomy (PCN).

Shock wave lithotripsy is performed as an extracorporeal treatment. This treatment utilizes a machine called a lithotripter that operates by directing ultrasonic or shock waves from outside the body, through the skin and tissue, and at the calculi or stones. Repeated shock waves apply stress to the stones, eventually breaking the individual stones into smaller pieces which can more easily pass through the urinary tract in urine. One benefit associated with shock wave lithotripsy is that it is a rather simple procedure. But it has been found that there is a relatively high rate of kidney stone recurrence following shock wave lithotripsy.

Transurethral lithotripsy or ureteroscopy represents one such alternative form of treatment. This treatment involves the use of small fiber optic instrument (endoscope) called an ureteroscope which allows access to the calculus in the ureter or kidney. The ureteroscope can be a rigid ureteroscope or more commonly, a flexible ureteroscope. The ureteroscope allows the medical professional to visualize the stone as the ureteroscope moves along the ureter or enters the kidney by way of the bladder and the urethra. Once the calculus is visualized, a basket-like device is used to grasp smaller stones and remove them. If the calculus is excessively large to remove as a single piece, it can be broken into smaller pieces by using laser energy.

The third form of treatment is percutaneous nephrolithotomy. This procedure is often used with relatively larger calculus that cannot be effectively treated with either ESWL or URS. Percutaneous nephrolithotomy involves nephrostomy; making an incision at the appropriate location, needling by paracentesis needle, positioning a guide wire through the paracentesis needle's lumen into the kidney under radiographic guidance, and then expanding perforated site. A nephroscope is then moved into the kidney via nephrostomy to visualize the calculus. Fragmentation of the calculus can be performed using an ultrasonic probe or laser.

Though these procedures have been commonly used, they are susceptible of certain short comings. For example, the ESWL procedure results in a relative large number of small calculi or small stones, while other procedures require a relatively narrow and long access route or are difficult to implement due to the inability to accurately capture the stones. In addition to, many crush pieces should be removed one by one in URS and PCNL procedure. The procedure time can also be excessively long, and can result in a relatively low "stone free rate." The recurrence rate can also be unacceptably high. And the potential patient complications (e.g., ischemia of the ureter, obstruction of ureter, back-flow and/or high-stress to the renal pelvis, infection of the urinary tract, and other possible injury) can be undesirably high.

Instances also arise, when performing operational procedures to gain access to calculus, as well as other procedures not specifically involving calculus, where it is desirable or necessary to advance a device into a narrow region in the living body. The operational procedure can be performed using an endoscope (ureteroscope), where the device is positioned in the instrument channel of the endoscope. Difficulties may arise in that the narrow region of the living body is excessively narrow and thus difficult to navigate through to gain access to the target site.

SUMMARY

One aspect of the disclosure here involves a method that comprises introducing a housing into a living body, wherein the housing possesses an interior with a rotatable impeller positioned in the interior of the housing, and the impeller includes an inlet and an outlet. The method also includes moving the housing in a lumen in the living body, positioning the housing at a narrowed region of the lumen in the living body, and rotating the impeller in the interior of the housing while the housing is located in the narrowed region of the lumen in the living body to draw fluid into the inlet and to expel the fluid out of the outlet so that the fluid which is expelled out of the outlet expands the narrowed region of the lumen in the living body to increase an interior size of the narrowed region to an expanded interior size.

In accordance with another aspect, a method involves introducing a housing into a channel in an endoscope, wherein the endoscope possesses a distal end and a longitudinally extending channel terminating at an outlet that opens adjacent the distal end of the endoscope, and wherein the housing possesses an inlet communicating with the interior of the housing in which is positioned a rotatable impeller, with the housing being moved along the channel to position the housing exterior of the channel at the distal end of the endoscope. The method also involves introducing the endoscope with the housing into a living body, moving the endoscope and the housing in a lumen in the living body, positioning the endoscope and the housing at a narrowed region of the lumen in the living body, introducing liquid into the channel in the endoscope so that the liquid flows along the channel and is discharged out of the outlet to expand the narrowed region of the lumen in the living body and increase an interior size of the narrowed region to an expanded interior size, and rotating the impeller in the interior of the housing while the housing is located in the narrowed region of the lumen in the living body to draw fluid into the inlet of the housing and to expel the fluid out of the outlet of the housing so that the fluid which is expelled out of the outlet of the housing expands the narrowed region of the lumen in the living body to increase an interior size of the narrowed region to an expanded interior size.

Other features and aspects of the methods disclosed here will become more apparent from the following detailed description considered with reference to the accompanying drawing figures in which like elements are designated by like reference numerals.

BRIEF DESCRIPTION OF DRAWINGS

FIG. 7A illustrates features which can be used to implement an operational procedure for expanding a narrowed region of a lumen in a living body without the suction head, and FIG. 7B illustrates features which can be used to implement an operational procedure for expanding a narrowed region of a lumen in a living body with the suction head.

FIGS. 8A and 8B illustrate aspects of an operational procedure which can be carried out using features such as those illustrated in FIG. 1 but without the suction head, and FIGS. 8C and 8D illustrate aspects of an operational procedure which can be carried out using features such as those illustrated in FIG. 1 but with the suction head.

FIG. 9 depicts another embodiment of features associated with the retrieving device of FIG. 1 that can be used to carry out another operational procedure for expanding a narrowed region of a lumen in a living body.

FIGS. 10A and 10B illustrate aspects of an operational procedure which can be carried out using features such as those illustrated in FIG. 1.

FIGS. 11A-11C illustrate kidneys under different conditions.

DETAILED DESCRIPTION

Set forth below is a detailed description of features and aspects of the retrieving system, device and operational procedure or method described here as examples of the disclosed invention. The systems, devices and operational procedures disclosed here for retrieving calculus have useful application to retrieve calculus/calculi located in the living body, including calculus/calculi located in the kidneys (kidney stones). The references below to calculus should be understood to refer to calculus in the singular as well as calculi in the plural. It is also to be understood that the methods, systems and devices disclosed here are not limited to retrieving calculus in a living body.

Generally speaking, the calculus retrieving device disclosed here, as represented by the several embodiments representing examples of the inventive retrieving device (and method), is configured to be positioned inside a living body at a position which will allow the retrieving device to suck-in or draw-in calculus to be retrieved. Set forth below is a detailed description of features and aspects of the calculus retrieving system, including a calculus retrieving device, and method described here by way of various embodiments representing examples of the disclosed inventions. The systems, devices and methods or operational procedures disclosed here for retrieving calculus have particular useful application to retrieve calculus located at places in the human body where removal of the calculus may otherwise be difficult due to, for example, the need to traverse a rather sharp curve to access the target site and/or the need to enter a rather narrow region to move toward and reach the target site.

Generally speaking, the calculus retrieving device disclosed here, as characterized by the several embodiments representing examples of the inventive calculus retrieving device (and method), is configured to be positioned inside a living body, at a position adjacent the location of calculus to be retrieved from the living body. The calculus (stone/stones) is drawn towards the retrieving device by creating a suction force in the retrieving device. After the calculus is retrieved, the calculus is retained or held by the retrieving device. The retrieving device can then be moved to the new location in the living body at which the retrieved calculus is to be repositioned. The retained calculus is subsequently released at the new location in the living body. Appropriate procedures (e.g., lithotripsy) can then be performed with respect to the calculus which has been moved. Alternatively, the retained calculus can be subsequently removed from the living body.

Figure 1:
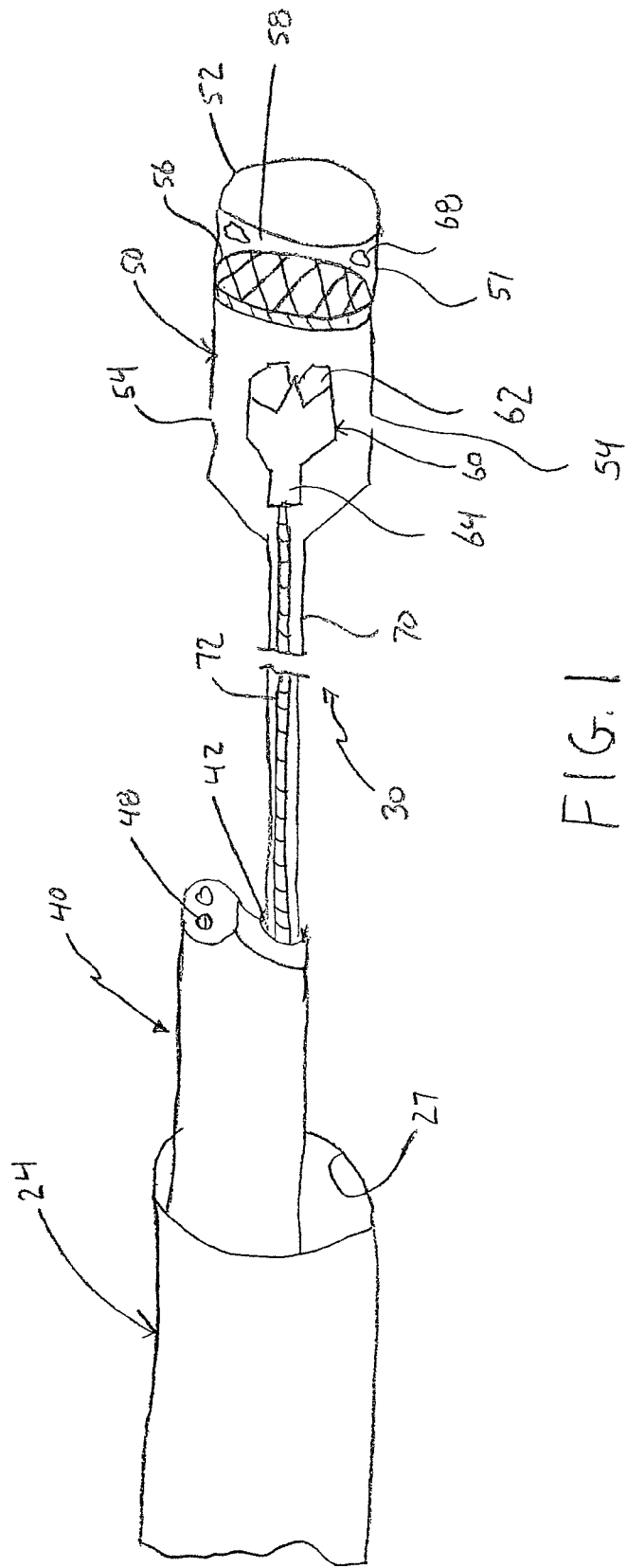
FIG. 1 is a schematic illustration of a system useful to retrieve calculus/calculi, including a retrieving device connected to an operation member (not shown in FIG. 1) through the intermediary of a lumen in an elongated body.

Turning now to the drawing figures, FIG. 1 illustrates, in a schematic fashion, a system 20 for retrieving and moving (removing) calculus (stone or stones) located in a living body. The system 20 includes a retrieving device 30 and an elongated body 40 possessing a lumen to deliver the retrieving device 30 to the desired place in the living body. In this illustrated embodiment representing one example of the system disclosed here, the elongated body 40 is an endoscope, particularly an ureteroscope. The endoscope or ureteroscope 40 includes a lumen or instrument channel 42, which receives a portion of the retrieving device 30, as will be described in more detail below. During use of the retrieving device 30, the ureteroscope 40 is introduced into the living body by way of a ureteral access sheath 24. The ureteroscope 40 passes through a lumen 27 in the ureteral access sheath 24.

Figure 3:
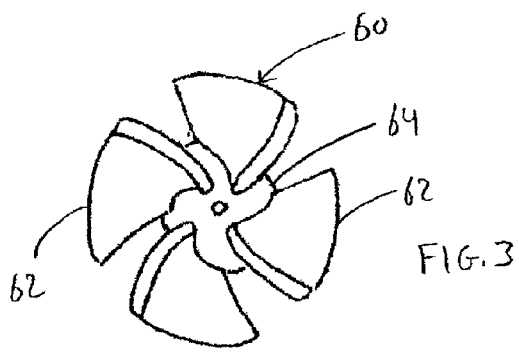
FIG. 3 is a front view of the impeller forming a part of the retrieving device shown in FIG. 2.
Figure 2:
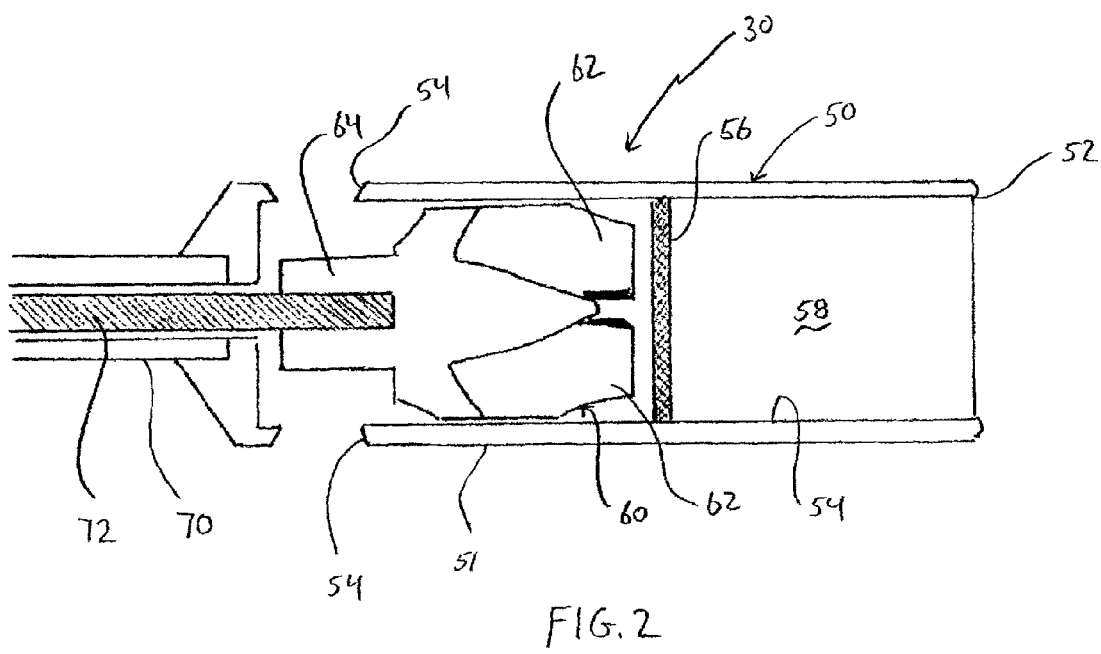
FIG. 2 is a side view, partially in cross section, of a retrieving device according to an embodiment representing an example of the retrieving device disclosed here.

Additional details and features associated with the calculus retrieving device 30 can be seen with reference to FIGS. 1, 2 and 3. The calculus retrieving device 30 includes a suction head 50 comprised of an elongated body or housing 51 having an open distal end 52. The housing 51 is a tubular housing possessing a lumen 55 defining an interior of the housing 51. The housing 51 can be configured as a cylindrical elongated body or housing.

The retrieving device 30 also includes a rotatable suction-producing part located inside the housing 51. In the illustrated embodiment, the rotatable suction-producing part is in the form of an impeller 60. As shown in FIGS. 1 and 3, the impeller is positioned in the housing 51 at a location spaced away from (i.e., proximally or rearwardly) the open distal end 52. An example of the impeller 60 is illustrated in FIG. 3. The impeller 60 includes a plurality of circumferentially spaced apart fins or blades 62 that are fixed to a central hub 64. The fins or blades 62 of the impeller 60 may be twisted fins or blades. The hub 64 is fixed or connected to a rotatably driven drive shaft 72 forming part of the device so that the drive shaft 72 and the impeller 60 rotate together as a unit. The impeller 60 is configured so that rotation of the impeller 60 in one rotational direction produces suction in the lumen 55 (in the interior) of the housing 51, while rotation of the impeller 60 in the opposite rotational direction produces the opposite result, namely an outwardly directed force out of the lumen 55. The blades 62 of the impeller 60 shown in FIGS. 2 and 3 are preferably twisted from the distal tip of the blades 62 (radially outermost tip of the blades) toward the bottom portion of the impeller where the blades are mounted. When the direction of the impeller rotation is the same as the twist direction of the blades 62, a suction force is generated. This direction of rotation of the impeller is referred to as overspin direction.

The drive shaft 72 that is connected to the hub 64 of the impeller 60 is positioned inside a shaft cover 70 and is covered by the shaft cover 70 which forms part of the device. In the illustrated embodiment, the drive shaft 72 is completely covered by the shaft cover 70. The shaft cover 70 is fixed to the housing 51 forming the suction head 50 so that movement of the shaft cover 70 results in movement of the suction head 50 (including the housing 51 and the impeller 60).

The housing 51 forming the suction head 50 includes a plurality of circumferentially spaced apart openings or through holes 54. These openings or through holes 54 are positioned closer to the proximal end of the housing 51 than the distal end of the housing 51. These openings or through holes 54 form outlets (an exhaust path) during operation of the retrieving device, as will become more apparent from the description below. That is, liquid (e.g., water) which has been drawn into the housing 51 of the suction head 50 during operation of the retrieving device 30 is exhausted or discharged out of the suction head 50 by way of the outlets 54.

The suction head 50 further includes a filter 56 located inside the housing 51 at a position between the distal end of the impeller 60 and the open distal end 52 of the suction head 50. This filter 56 is a disc-shaped mesh member that allows the passage of fluid (e.g., liquid such as water), while also preventing the passage of calculus which has been retrieved through operation of the retrieving device 30. The filter 56 possesses an outer periphery (outer circumferential surface) in contact with the inner periphery of the suction head 50. The filter 56 is positionally fixed within the interior of the housing 51 forming the suction head 50.

The suction head 50 also includes a retrieval space 58 located between the filter 56 and the open distal end 52 of the housing 51. As will be described in more detail below, this retrieval space 58 is configured to receive calculus which has been retrieved as a result of the operation of the retrieving device 30.

During operation of the retrieving device 30, the suction head 50 is located at a position in a living body to retrieve calculus. That is, the suction head 50 is positioned relative to the calculus to be retrieved such that during operation of the retrieving device 30, the calculus will be drawn towards (sucked towards) the suction head 50. When the suction head 50 is properly positioned relative to the calculus to be retrieved, the impeller 60 is rotatably driven through operation of a driving device 28 (e.g., a geared motor) connected to the drive shaft 72. The drive device rotates the drive shaft 72, which in turn rotates the impeller 60. The impeller 60 is rotatably driven in a direction to create suction in the interior of the housing 51 that draws calculus toward the open distal end 52 of the suction head 50. The suction force created by the rotation of the impeller 60 draws relatively smaller calculus (schematically shown in FIG. 1 and identified as 68) through the open distal end 52 of the suction head and into the retrieval space 58 in the housing 51. The suction force created by the rotation of the impeller 60 can also draws relatively larger calculus into contact with the distal end of the suction head 50. That is, calculus possessing an outer dimension larger than the size of the open distal end 52 of the suction head 50 can nevertheless be drawn towards the suction head 50 and retained by the suction head 50 by creating sufficient suction force in the interior of the housing 51 that holds the relatively larger calculus in contact with the distal end of the suction head 50.

Thus, by positioning the suction head 50 in the living body so that the open distal end 52 of the suction head 50 is located at a position that will allow the calculus (i.e., calculus to be retrieved) to be drawn-into or sucked into the retrieval space 58 upon rotational operation of the impeller 60, it is possible to retrieve calculus and hold the retrieved calculus either in the retrieval space 58 or at the distal end of the suction head 50. As the impeller 60 is rotated to draw calculus toward the suction head 50, liquid (e.g., water) is drawn into the retrieval space 58 by way of the distal open end 52 of the suction head 50. This liquid is passes through the filter 56, and is exhausted or discharged outside the housing 51 of the suction head 50 through the openings or through holes 54. On the other hand, the filter 56 is sized to ensure that calculus which is drawn into the retrieval space 58 of the suction head 50, does not pass through the filter 56. The rotational operation of the impeller 60 thus causes liquid flow in which liquid enters the distal open end 52 of the suction head 50, passes through the filter 56, and exits through the through holes or openings 54 in the suction head 50. Depending upon operation of the impeller 60, the liquid exhausted through the openings or through holes 54 can also be at least partially drawn back into the interior of the suction head 50, thus creating a rather turbulent and continuous liquid cycle in which the same liquid is repeatedly drawn into the suction head, exhausted through the suction head 50, drawn into the suction head, etc. This turbulent and continuous liquid cycle can help facilitate retrieval of calculus in the retrieval space 58 of the suction head 50. This is because the suction force per rotation of the impeller is increased. In addition, the calculus tends to float, making it easier to draw-in or retrieve the calculus. When drawing-in calculus in a narrow lumen in a living body (e.g. ureter), the continuous liquid cycle helps prevent fluid surrounding calculus from drying up.

Set forth next is a description of ways in which the system for retrieving calculus disclosed here can be used, as well as a description of operational procedures performed using the calculus retrieving system. Calculus that is not excessively large can be retrieved and removed from the living body using the retrieving system, device and operational procedures or methods disclosed here. But it is sometimes necessary or desirable to break-up calculus located in a living body. For instance, if the calculus is relatively large (e.g., larger than the ureter diameter), it is not possible to remove the calculus from the living body. In such situations, it would be desirable to break-up the calculus into smaller size pieces. This can oftentimes be accomplished using lithotripsy. Circumstances may make it difficult to perform lithotripsy to break-up calculus in the living body. For example, the calculus may be located at a place where damaged tissue exists, for example in a portion of the ureter in which there is damaged tissue. Alternatively, the calculus may be located in a portion of the living body (e.g., ureter) that is rather small in size (i.e., a narrow space) and difficult to access with appropriate instrumentation and equipment for performing lithotripsy (e.g., a lower calix). The retrieving system and retrieving device disclosed here can be used to retrieve calculus, moving the retrieved calculus to a new (different) location which presents a larger space (e.g., the renal pelvis or an upper calix) to perform lithotripsy or which presents a region where there is normal (non-damaged tissue) tissue.

Figure 4:
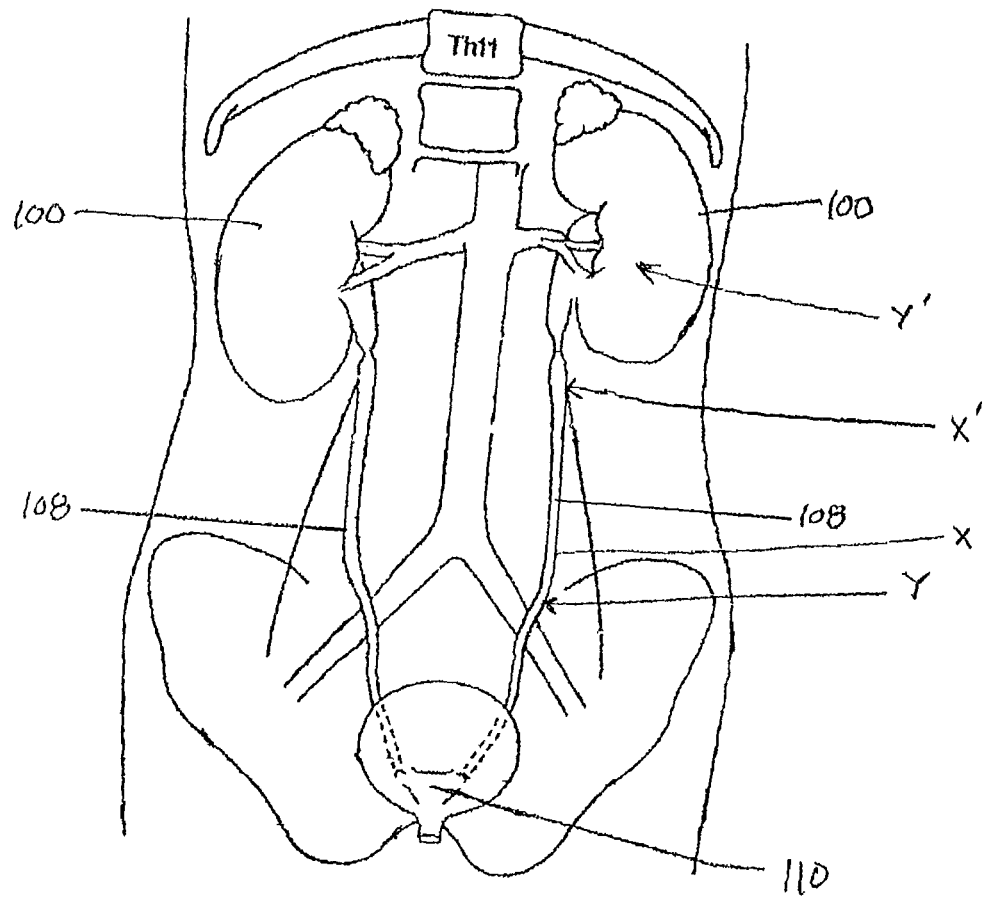
FIG. 4 is a schematic illustration of a portion of the human anatomy, including the urinary tract.

As explained, the retrieving device and system disclosed here can be used to retrieve calculus from a living body and remove the retrieved calculus from the living body, and can also be used to retrieve calculus from one place in the living body, move the retrieved calculus to a new (different) place in the living body where, for example, lithotripsy can be more easily performed to break-up the calculus, and then release the retrieved and moved calculus at the new location. By way of example, and with reference to FIG. 4, it is possible to retrieve calculus at the location X in the ureter (representing an example of a region of narrow size or damaged tissue) and move the retrieved calculus to the position X' in the ureter (representing an example of a region of larger size or normal non-damaged tissue). It is also possible to retrieve calculus at the location Y (representing an example of a region of narrow size or damaged tissue) and move the retrieved calculus to the position Y' in the kidney 100 (representing another example of a region of larger size or normal non-damaged tissue).

Figure 6:
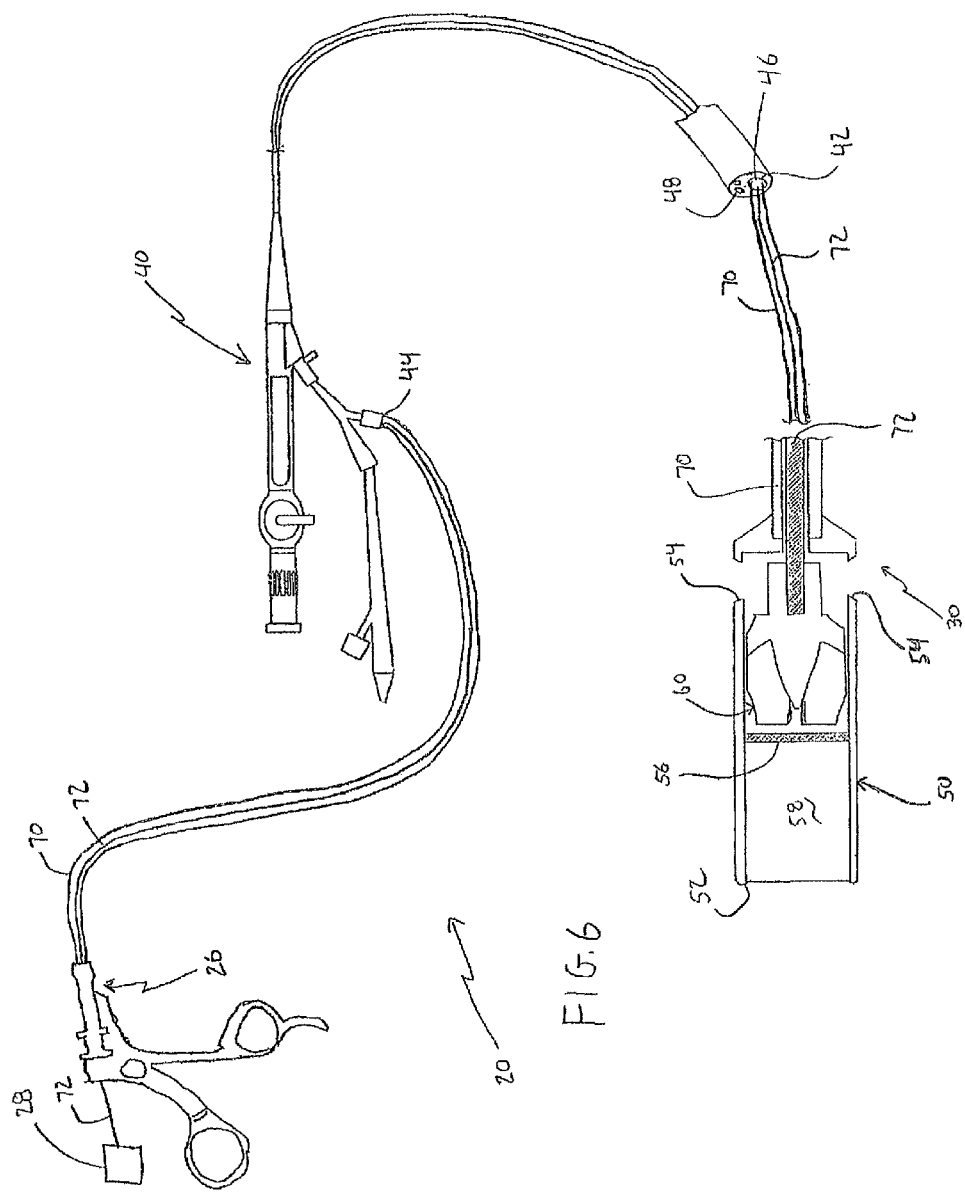
FIG. 6 is a schematic illustration of the retrieving system, including the retrieving device connected to the operation member through the intermediary of an elongated body such as an endoscope (ureteroscope).

To retrieve (and move) the calculus, a retrieving system such as the retrieving system 20 shown in FIG. 6 can be used. Specifically, the calculus retrieving device 30 is used, together with the operating member 26 and the endoscope 40 (ureteroscope). The operating member 26 is connected to the shaft cover 70, so that operation of the operating member 26 causes the shaft cover 70 to move. That is, the operation of the operating member 26 causes the shaft cover 70 to axially move, which in turn causes the suction head 50 (including the impeller 60 and the filter 56) to also axially move. FIG. 6 schematically illustrates that the drive shaft 72 positioned within and extending along the axial length of the shaft cover 70 is connected to the driving device 28. Operation of the driving device 28 rotates the drive shaft 72, which in turn rotates the impeller 60 positioned in the housing 51 of the suction head 50 of the calculus retrieving device 30. As shown in FIG. 6, the shaft cover 70 and the drive shaft 72 extend from the operating member 26, enter an inlet 44 of the instrument channel 42 in the ureteroscope 40, pass through the ureteroscope 40, and exit at an outlet at the distal end portion 46 of the ureteroscope 40.

In use, the shaft cover 70 is connected to the housing 51 of the suction head 50, and the proximal end of the shaft cover 70 and the drive shaft 72 are inserted into the outlet of the instrument channel 42 at the distal end portion 46 of the ureteroscope 40. The shaft cover 70 and the drive shaft 72 are pushed through the lumen (instrument channel 42) in the ureteroscope 40 until the proximal end of the shaft cover 70 and the proximal end of the drive shaft 72 exit out of the inlet 44 of the ureteroscope. The proximal end of the drive shaft 72 is then connected to the driving device 28, while the proximal end of the shaft cover 70 is fixed to the operating member 26.

In the case of the endoscope 40 being an ureteroscope, the ureteroscope is preferably a flexible ureteroscope. The ureteroscope 40 includes a viewing system that includes an objective lens or camera 48 schematically illustrated in FIG. 1 (and FIG. 6). In a known manner, this provides a field of view for the user or operator to facilitate carrying out the procedure involving locating calculus, retrieving the calculus, moving the calculus to the new location and releasing the calculus at the new location.

Figure 5:
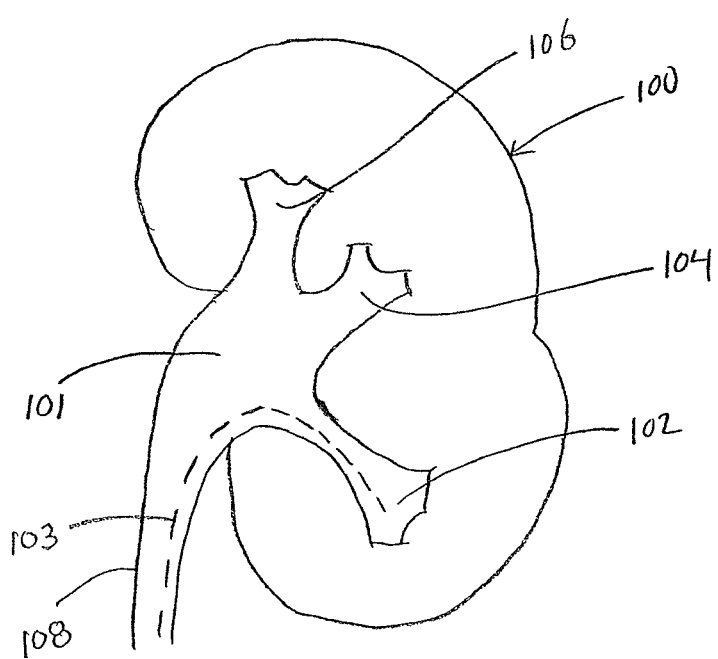
FIG. 5 is a schematic illustration of a human kidney, illustrating the renal pelvis, a lower calix (lower renal calix), a middle or intermediate calix (middle or intermediate renal calix), and an upper calix (upper renal calix).

FIG. 5 schematically illustrates a kidney 100 and depicts various sections or regions of the kidney 100 including the renal pelvis 101, a lower calix 102 (lower renal calix), a middle or intermediate calix 104 (middle or intermediate renal calix) and an upper calix 106 (upper renal calix). It is sometimes desirable to operate the retrieving system to access the lower calix 102 of the kidney to retrieve calculus located in the lower calix. To reach calculus in the lower calix 102 requires access by way of the ureter 108 along a path generally indicated by the dotted line 103 in FIG. 5. This path 103 can be rather difficult to navigate due to, for example, the relatively narrow entrance to the lower calix 102. Similarly, the renal pelvis 101 itself can be difficult to navigate because the size of the renal pelvis can be rather small. Another aspect of the disclosure here involves operational procedures or methods for expanding lumens associated with access to an in the kidney, including the renal pelvis 101, the lower calix 102, the ureter 108, etc. In this way, access to the location of the calculus, for example the lower calix 102, is improved. These methods or operational procedures are not limited to use in accessing the lower calix. Indeed, the methods can be used in other regions of the living body to help facilitate navigation to a target site in the living body such as other locations where an object to be captured may be located.

Part of the difficulty associated with navigating to or through rather narrow regions in the living body, such as the entrance region to the lower calix, when using the retrieving system and device described above is that parts of the system and device may not be well suited to traversing through a narrow region. For example, the suction head of the retrieval device 30 and the tip portion of the endoscope (ureteroscope) are typically not flexible and pliable, and so are not well suited to being navigated through a narrowed region. Set forth below is a description of several operational procedures or methods which make it possible for the suction head and endoscope (ureteroscope) to better navigate through narrow or narrowed regions (hereinafter referred to as "narrowed region(s)".

The embodiments disclosed below involve different ways of expanding or increasing the size of the narrowed region in the living body. Thus, the expanding methods described below can involve expanding of increasing the size of the renal pelvis 101, expanding or increasing the size of the entrance into the lower calix 102, expanding or increasing the size of the ureter 108, etc.

The embodiment illustrated in FIG. 7A includes a perfusion system to introduce liquid into the narrowed region to expand the narrowed region or increase the size of the narrowed region. In this illustrated embodiment, the perfusion system is comprised of the endoscope 40 (ureteroscope) forming a part of the retrieving system described above. That is, the endoscope can be used as a part of the perfusion system to deliver liquid to the narrowed region.

The endoscope 40 is connected to a source of liquid. In this embodiment, the source of liquid is connected to the instrument channel 42 of the endoscope via the inlet 44. FIG. 7A illustrates two examples of sources of liquid—a liquid-containing bag 300 and a liquid-containing syringe 200. Of course, other sources of liquid are possible. The liquid can be any suitable liquid such as water, saline or contrast agent.

An example of a method or operational procedure performed to expand or increase the size of the narrowed region in the living body through use of the perfusion system shown in FIG. 7A is described below with reference to FIGS. 8A and 8B. To begin, the distal end of the endoscope 40 (ureteroscope) is introduced into the living body such as in the manner previously described above. The endoscope 40 is then moved along the living body where it passes through the lumen in the bladder 110 (FIG. 4) and eventually enters the lumen in the ureter 108. The endoscope 40 is further advanced until the distal portion of the endoscope 40 enters the renal pelvis 101 as generally illustrated in FIG. 8A.

The liquid source (e.g., the liquid-filled bag 300 or the liquid-filled syringe 200) fluidly communicates with the instrument channel 42. The liquid source can be connected to the proximal end of the instrument channel 42 before or after the distal end of the endoscope 40 is introduced into the living body. While the distal end of the endoscope 40 is positioned in the renal pelvis 101, liquid from the liquid source enters the instrument channel 42 and flows along the instrument channel 42. The liquid in the instrument channel 42 is ultimately discharged from the instrument channel 42 by way of the outlet at the distal end portion 46 of the endoscope 40. The liquid discharged from the instrument channel 42 of the endoscope 40 enters the renal pelvis 101. As illustrated in FIG. 8B, the liquid entering the renal pelvis 101 applies an outwardly directed force (indicated by the arrows), expanding or increasing the size of the lumen in the living body (i.e., increasing the size of the renal pelvis) as generally depicted in FIG. 8B. This expanded or enlarged interior of the renal pelvis 101 allows the to-be-introduced suction head 50 to maneuver or navigate in the renal pelvis in an easier manner, while also providing an expanded region that makes it easier to retrieve calculus in the renal pelvis. The liquid introduced into the kidney primarily expands the interior size of the renal pelvis, but may also expand the interior size of other parts of the kidney such as the calices, depending upon the amount of liquid introduced into the kidney. The expansion of the renal pelvis occurs before possible expansion of other parts of the kidney.

The amount by which the internal size of the kidney (renal pelvis) expands during introduction of the liquid depends on a variety of factors such as the amount of urine retention, the clinical condition of the kidney, the amount of liquid introduced into the kidney, etc. FIGS. 11A-11C illustrate three conditions of a kidney. FIG. 11A illustrates the kidney in an empty or vacant condition, FIG. 11B depicts the kidney when expanded by urine or pumped liquid, and FIG. 11C illustrates the kidney expanded even further by pumped liquid or the kidney which is in a hydronephrosis condition caused by an obturation of the ureter (especially a site of transition from the ureter to the kidney) associated with the presence of ureteral stones. The condition shown in FIG. 11 A represents a normal and safe condition of the kidney, while the condition shown in FIG. 11B is also a usual and safe condition, though the volume inside the kidney is slightly larger at about 5 mL due to the expansion associated with urine in the kidney and/or liquid pumped into the liquid. FIG. 11C shows a condition of the kidney expanded even further by pumped liquid or the kidney being in the hydronephrosis condition caused by the obturation of the ureter so that the volume inside the kidney is increased more than shown in FIG. 11B. In the case of a patient shown in FIG. 11C, the expanded volume inside the kidney can vary between 10 mL up to 30 mL-40 mL in the case of a patient with a severe stone condition (hydronephrosis condition). The typical example of the severe stone condition is an impacted stone at the ureter. The above volumes of the expanded kidney means the total content of the expanded renal pelvis and the expanded renal calices, for instance, after positioning the ureteroscope 40 in a upper ureter, the operator can draw about 5 mL of the fluid from the expanded kidney shown in FIG. 11B by the syringe attached to the inlet 44 of the ureteroscope 40. This drawing begun from the condition in FIG. 11B is automatically stopped when the kidney is shrunk to the vacant condition shown in FIG. 11A.

It is possible to configure or size the outer diameter of the endoscope 40 so that it relatively closely matches or is the same as the inner diameter of the ureter 108 as generally indicated at 120 in FIG. 8B. An advantage of matching the outer diameter of the endoscope 40 to the inner diameter of the ureter 108 is that a seal is created between the outer surface of the endoscope 40 and the inner surface of the ureter 108 so that liquid which has been introduced into the renal pelvis 101 will remain in the renal pelvis 101 so that the renal pelvis 101 is maintained in the expanded condition.

The description above describes the endoscope being used as the mechanism to introduce liquid into the renal pelvis 101. According to a preferred operational procedure, the liquid is introduced into the renal pelvis 101 while the suction head 50 (with the drive shaft 72 and the shaft cover 70) is mounted in the endoscope 40. One way of carrying out this method or operational procedure is as follows. First, before introducing the endoscope 40 into the living body, a known three-way stopcock 79 (T-shaped stopcock) is connected to the inlet 44 at the proximal end of the endoscope 40. The suction head 50 (with the drive shaft 72 and the shaft cover 70) is then mounted in the instrument channel 42 of the endoscope 40 so that the proximal ends of the drive shaft 72 and the shaft cover 70 extend out one of the ports of the three-way stopcock 79. This is accomplished by inserting the proximal end of the drive shaft 72 and the shaft cover 70 into the outlet at the distal end of the instrument channel 42 in the endoscope 40, and advancing the drive shaft 72 and the shaft cover 70 along the instrument channel 42 until the proximal ends of the drive shaft 72 and the shaft cover 70 extend out one of the ports of the three-way stopcock 79. The instrument channel 42 is sized relative to the shaft cover 70 so that a space exist between the inner surface of the instrument channel 42 and the outer surface of the shaft cover 70. The source of liquid (e.g., 300 or 200) is then connected to another one of the ports of the three-way stopcock 79. The endoscope 40 with the suction 50 (and the drive shaft 72 and the shaft cover 70) is inserted into the living body and is advanced toward the target area in the living body (e.g., renal pelvis). This can be done by inserting the endoscope 40 with the suction 50 (and the drive shaft 72 and the shaft cover 70) into the living body, moving the endoscope 40 in the living body and into the ureter as described above, and ultimately positioning the outlet of the endoscope 40, along with the suction head 50, in the renal pelvis in the renal pelvis 101 as generally shown in FIGS. 8C and 8D. Liquid from the source (e.g., 300 or 200) is then pumped into the renal pelvis 101 by way of the instrument channel 42. The liquid is able to flow along the instrument channel 42 despite the presence of the drive shaft 72 and the shaft cover 70 in the instrument channel 42 because of the space 77 that exists between the inner surface of the instrument channel 42 and the outer surface of the shaft cover 70 shown in FIG. 7B. The liquid is delivered from the source (e.g., 300 or 200) to the renal pelvis 101 by way of the instrument channel 42 by pushing the plunger on the liquid-containing syringe 200 or by using an IV stand to hold the liquid-containing bag 300. It is also possible to use a pump configured for the perfusion system of the endoscope. After liquid is introduced into the renal pelvis, the suction head 50 can then be operated in the manner described above to retrieve calculus in the renal pelvis. Because the size of the renal pelvis 101 is enlarged by the introduction of the liquid, it is easier to navigate the suction head 50 in the renal pelvis and position the suction head 50 at a place to retrieve calculus. That is, the calculus is more accessible. If desired, the suction head 50 located in the renal pelvis 101 can be navigated into the lower calix 102 to retrieve calculus in the lower calix.

FIG. 9 illustrates another way to expand or enlarge a narrowed region in a living body (in a lumen in a living body). In this embodiment, the suction head 50 is used to expand the narrowed region through use of liquid that is already present and/or previously introduced by way of the endoscope as described above and shown in FIGS. 8C and 8D. The method or operational procedure shown in FIGS. 9, 10A and 10B can involve introducing liquid into the target area (e.g., using the endoscope as shown in FIGS. 7B, 8C and 8DB) and then operating the suction head to use such liquid to expand the narrowed region. The method or operational procedure shown in FIGS. 9, 10A and 10B can also involve using liquid (e.g., urine) already present in the kidney and operating the suction head to use such already present liquid to expand the narrowed region. FIG. 9 illustrates the suction head 50 positioned in a narrowed region of the kidney. In this illustrated example, the suction head 50 is positioned in the narrowed region at the entrance to the lower calix 102. This positioning of the suction head 50 is generally depicted in FIG. 10A.

According to the operational procedure illustrated in FIG. 9, the suction head 50 is positioned in the narrowed region at the entrance to the lower calix 102. The suction head 50 can be moved to this location using the procedure described above (i.e., by traversing the bladder, the ureter and the renal pelvis). When the suction head 50 is at the narrowed entrance to the lower calix 102, the suction head 50 is operated to cause the impeller (the impeller 60 shown in FIGS. 1 and 2) inside the housing of the suction head 50 to rotate. As described above, this rotation of the impeller creates a suction force which draws liquid into the interior of the housing by way of the inlet at the front end of the housing, while at the same time expelling liquid from the interior of the housing by way of the outlets 54. As illustrated in FIGS. 9 and 10B, the liquid expelled from the interior of the housing of the suction head 50 by way of the outlets 54 creates a radially outwardly directed force that is perpendicular (inclusive of substantially perpendicular) to the wall of the narrowed region of the lumen in the living body (i.e., the narrowed entrance region to the lower calix). As mentioned above, the liquid that is sucked into the housing of the suction head and that is expelled by way of the outlets 54 is liquid that is already present and/or has been introduced by way of the endoscope 40 (e.g., the instrument channel of the endoscope). The description above and the illustrations in FIGS. 8C and 8D show that the liquid is introduced into the renal pelvis. It is also possible, for example when expanding a narrowed target region other than the renal pelvis in general, to position the distal end of the endoscope at the narrowed target region so that the liquid is introduced into the narrowed target region. As an example, when expanding the narrowed entrance to the lower calix such as shown in FIGS. 10 and 10B, the distal end of the endoscope can be positioned at the narrowed entrance to the lower calix so that the liquid is introduced into the narrowed entrance to the lower calix.

Also, the description above explains that the liquid is introduced into the target region, and then the suction head 50 is operated. It is also possible to operate the suction head 50 while the liquid is being delivered to the target region.

It is possible to vary the speed of rotation of the impeller to alter the amount of expansion of the lumen in the living body and/or to alter the amount of calculus retrieved by the suction head 50. For example, the impeller can be operated at a relatively high rotational speed to expand or increase the size of the narrowed regions, and to rotate at a relatively lower rotational speed to draw calculus into the interior of the housing of the suction head 50 by way of the inlet of the housing. The relatively higher rotational speed for expanding the narrowed region may create a lot of turbulence around the suction head and so the suction head may not be so well suited to drawing calculus into the interior of the housing by way of the inlet. On the other hand, when the rotational speed of the impeller is reduced after having expanded the narrowed region, calculus is more likely to be drawn into the interior of the housing of the suction head 50. One preferred method or operational procedure involves rotating the impeller of the suction head 50 at a relatively higher rotational speed to expand the narrowed region, navigating the suction head 50 pass the expanded narrowed region while still rotating the impeller at the relatively higher rotational speed, then reducing the rotational speed of the impeller to a relatively lower rotational speed so that the suction head is able to draw calculus into the housing of the suction head 50.

The operational procedures described above and shown in FIGS. 7A, 7B and 8A-8D involve gradually increasing the amount (volume) of liquid introduced into the kidney to so that the size of the interior of the kidney and the internal pressure inside the kidney gradually increase. This same gradual increase in the amount (volume) of liquid introduced into the interior of the kidney is not necessary in the operational procedure shown in FIGS. 9, 10A and 10B. Instead, in the version of the method shown in FIGS. 9, 10A and 10B, the amount of liquid introduced into the kidney does not change. That is, it is not necessary to introduce liquid into the kidney because the method shown in FIGS. 9, 10A and 10B primarily relies on liquid already present in the kidney (urine and/or perfusion water/saline). The reason for this difference is that the method shown in FIGS. 9, 10A and 10B creates a local relatively high pressure by the rotating impeller, and this local relatively high pressure can extend or expand the wall of the narrowed region. By virtue of this manner of expansion, the internal pressure of the kidney, especially around an undersurface of the renal calix (i.e. a papilla renalis), tends not to be increased. It is important to avoid increasing the internal pressure around the papilla renalis as a way of preventing an adverse fluid flow from the lumen of the kidney to the inside of the kidney tissue. This adverse current is one of the major factors of infection following a surgical procedure.

The method or operational procedure illustrated in FIGS. 7B, 8C and 8D can be used to expand a narrowed region especially for the renal pelvis. That is, the embodiment illustrated in FIGS. 7B, 8C and 8D can be implemented by positioning the suction head in the renal pelvis 101 and then introducing the liquid into the renal pelvis. Similarly, the operational procedure or method shown in FIGS. 9, 10A and 10B can be used to expand a narrowed region especially for the lower calix. That is, the embodiment illustrated in FIGS. 9, 10A and 10B can be implemented by positioning the suction head in the entrance to the lower calix 102, and then introducing the liquid. It is to be recognized that the different operational procedures described above and illustrated in FIGS. 7-10B are not necessarily limited to use in the respective illustrated and described regions, and are usable in other areas of the kidney to expand or widen narrowed regions.

For instance, in the patient of the ureteral stone disease, the impacted stone causes a narrow ureter, a nontortuous ureter and a transient obstructed ureter. Such changes of shapes of the ureteral lumen can cause difficulties in conveying the device (the ureteroscope 40 and the ureteroscope 40 with the retrieving device 30). Because the wall of the ureter is relatively soft and expandable the above expansion mechanism can be applied to widen such narrowed region of the ureter. In addition, some damaged ureteral walls have an edema. Such damaged ureter tends to lose a ductility and/or a lubricity and/or a toughness of the ureteral wall so general dilational procedure (e.g., inserting a rod-shaped dilator) can relatively easily damage the ureter (e.g., plasmotomy of the ureter). When the rod-shaped dilator is inserted into the ureteral lumen toward the kidney, the resistance between the inner surface of the ureteral wall and an outer surface of the dilator is generated as lengthwise direction (an elongated axial direction of the ureter). Such the vertical force has a risk to cause the plasmotomy of the damaged ureter. On the other hand, the liquid expelled from the interior of the housing of the suction head 50 by way of the outlets 54 creates a radially outwardly directed force, so the expansion by using the suction head 50 shown in FIG. 9 is safer than the general dilational procedure.

The method or operational procedure to expand the narrow ureter is the same as described above. In short, at first the distal end of the ureteroscope 40 with the suction head 50 is positioned in front of the narrowed region of the ureter 108, and then the driving device 28 rotates the impeller 60 to create the exhaust flow through the outlets 54, and finally the ureteroscope 40 with the suction head 50 is moved to pass the narrowed region of the ureteral lumen while maintaining the exhausting. In many cases, before inserting of the ureteroscope 40 with suction head 50, the ureteral lumen is filled by the fluid (e.g., the urine and/or the perfusion fluid) so the suction head 50 can easily create the objective radially outwardly directed force. Of cause, if the amount of the fluid of the ureteral lumen is not adequate, the additional liquid can be delivered from the source (e.g., 300 or 200) to the ureteral lumen by way of the instrument channel 42 by pushing the plunger on the liquid-containing syringe 200 or by using an IV stand to hold the liquid-containing bag 300 shown in FIG. 7B.

In the embodiments described above, the endoscope 40 and the suction head 50 operate as liquid-driven expanders that expand the size of a narrowed region in the living body. The methods or operational procedures described above are carried out to expand narrowed regions in the kidney. This is done by increasing the pressure within the kidney, either by introducing sufficient liquid into the kidney or by operating the impeller. It is preferable that the expansion of the narrowed region be carried out to maintain the average internal pressure of the kidney (narrowed region of the lumen in the living body) so that it does not exceed 100 $cmH_2O$, more preferably does not exceed 50 $cmH_2O$, during the expansion of the narrowed region of the lumen in the living body. Thus, when liquid is introduced into the renal pelvis such as shown in FIGS. 7A, 7B and 8A-8D, and/or when the impeller of the suction head 50 is operated in the manner shown in FIGS. 9, 10A and 10B, the average internal pressure of the narrowed region of the lumen in the living body is maintained so as not to exceed 100 $cmH_2O$, more preferably not to exceed 50 $cmH_2O$ during expansion of the narrowed region of the lumen in the living body.

To help ensure that the average internal pressure of the narrowed region of the lumen in the living body does not exceed the preferred maximum described above, a sensor can be provided. As an example, the suction head 50 (housing of the suction head) can be provided with a sensor 57 such as shown in FIGS. 6 and 9 to sense the pressure in the living body to ensure that the internal pressure does not exceed a desired maximum pressure (100 $cmH_2O$, more preferably 50 $cmH_2O$). The sensor 57 is mounted on the outer surface of the suction head 50 (housing of the suction head) and is connected to a display 59 located outside the living body. The connection of the sensor 57 to the display 59 can be by way of a cable that extends from the sensor 57, is fixed to the outer surface of the shaft cover 70, passes through the instrument channel 42 of the endoscope 40 and exist out of the proximal end of the instrument channel 42 as shown in FIG. 6.

During operation of the suction head 50 (rotation of impeller) shown in FIGS. 9, 10A and 10B, the volume of the liquid that is drawn into the inlet of the housing of the suction head 50 and the volume of the liquid that is expelled out of the outlet of the suction head 50 are substantially equal so that the overall volume of the fluid existing in the lumen of the living body is controllable. This substantial equality of the liquid that is drawn into the inlet of the housing of the suction head 50 and the volume of the liquid that is expelled out of the outlet of the suction head 50 applies also to the operational procedure shown in FIGS. 7B, 8C and 8D.

The detailed description above describes devices and methods for retrieving calculus from parts of a living body such as the ureter and the renal pelvis, and for expanding narrowed regions of the living body in advance of or during the calculus retrieval operation or method. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A method comprising:
introducing a housing into a living body, the housing possessing an interior with a rotatable impeller positioned in the interior of the housing, the impeller including an inlet and an outlet;
moving the housing in a lumen in the living body;
positioning the housing at a narrowed region of the lumen in the living body; and
rotating the impeller in the interior of the housing while the housing is located in the narrowed region of the lumen in the living body to draw fluid into the inlet and to expel the fluid out of the outlet so that the fluid which is expelled out of the outlet expands the narrowed region of the lumen in the living body to increase an interior size of the narrowed region to an expanded interior size.

2. The method according to claim 1, further comprising moving the housing toward a target site at which is located the calculus while continuing to rotate the impeller to maintain the expanded interior size of the narrowed region.

3. The method according to claim 2, further comprising positioning the housing at the target site while continuing to rotate the impeller so that the rotation of the impeller draws the calculus through the inlet and into the interior of the housing.

4. The method according to claim 3, wherein the impeller is rotated at a first rotational speed to expand the interior size of the narrowed region to an expanded interior size, and the impeller is rotated at a second rotational speed to draw the calculus through the inlet and into the interior of the housing, the second rotational speed being different from the first rotational speed.

5. The method according to claim 3, wherein the impeller is rotated at a first rotational speed to expand the interior size of the narrowed region to the expanded interior size, and the impeller is rotated at a second rotational speed to draw the calculus through the inlet and into the interior of the housing, the first rotational speed being greater than the second rotational speed.

6. The method according to claim 1, wherein the positioning of the housing at the narrowed region of the lumen in the living body includes positioning the housing in a ureter of the living body at which the narrowed region is located.

7. The method according to claim 1, wherein the living body includes a ureter connected to a kidney in the living body, the ureter including a lumen that opens into a renal pelvis of the kidney, and the positioning of the housing at the narrowed region of the lumen in the living body includes positioning the housing at an entrance to the lower calix, the entrance being located between the renal pelvis and the lower calix, the narrowed region being located in the entrance.

8. The method according to claim 1, wherein the positioning of the housing at the narrowed region of the lumen in the living body includes positioning the housing at a renal pelvis of a kidney, at a renal calix of the kidney or at an entrance to the renal calix of the kidney, and rotating the impeller in the interior of the housing to maintain an average internal pressure of the narrowed region of the lumen in the living body that does not exceed 100 cmH$_2$O during the expansion of the narrowed region of the lumen in the living body.

9. The method according to claim 1, wherein the impeller in the interior of the housing is connected to a shaft, the introduction of the housing into the living body being performed by introducing an ureteroscope into the living body while the shaft is located in an instrument channel of the ureteroscope and the housing is positioned distal of a distal end of the ureteroscope.

10. The method according to claim 1, further comprising preventing the calculus that is drawn into the interior of the housing from contacting the impeller.

11. The method according to claim 10, wherein the calculus that is drawn into the interior of the housing is prevented from contacting the impeller by a filter located in the interior of the housing at a position between the inlet and the impeller.

12. The method according to claim 1, wherein a first volume of the fluid that is drawn into the inlet and a second volume of the fluid that is expelled out of the outlet are substantially equal so that a whole volume of the fluid existing in the lumen of the living body is controllable.

13. A method comprising:
introducing a housing into a channel in an endoscope, the endoscope possessing a distal end and a longitudinally extending channel terminating at an outlet that opens adjacent the distal end of the endoscope, the housing possessing an inlet and an outlet both communicating with the interior of the housing in which is positioned a rotatable impeller, the housing being moved along the channel to position the housing exterior of the channel at the distal end of the endoscope;
introducing the endoscope with the housing into a living body;
moving the endoscope and the housing in a lumen in the living body;
positioning the endoscope and the housing at a narrowed region of the lumen in the living body;
introducing liquid into the channel in the endoscope so that the liquid flows along the channel and is discharged out of the outlet to expand the narrowed region of the lumen in the living body and increase an interior size of the narrowed region to an expanded interior size; and
rotating the impeller in the interior of the housing while the housing is located in the narrowed region of the lumen in the living body to draw fluid into the inlet of the housing and to expel the fluid out of the outlet of the housing so that the fluid which is expelled out of the outlet of the housing expands the narrowed region of the lumen in the living body to increase an interior size of the narrowed region to an expanded interior size.

14. The method according to claim 13, wherein the impeller in the interior of the housing is connected to a shaft, the introduction of the endoscope with the housing into the living body being performed by introducing the endoscope into the living body while the shaft is located in an instrument channel of the endoscope and the housing is positioned distal of a distal end of the ureteroscope, and wherein introducing liquid into the channel in the endoscope so that the liquid flows along a clearance between an outer surface of the shaft and an inner surface of the instrument channel of the endoscope.

15. The method according to claim 13, wherein the positioning of the endoscope at the narrowed region of the lumen in the living body includes positioning the endoscope in a ureter of the living body at which the narrowed region is located.

16. The method according to claim 13, wherein the living body includes a ureter connected to a kidney in the living body, the ureter including a lumen that opens into a renal pelvis of the kidney, and the positioning of the endoscope at the narrowed region of the lumen in the living body includes positioning the endoscope at an entrance to the lower calix, the entrance being located between the renal pelvis and the lower calix, the narrowed region being located in the entrance.

17. The method according to claim 13, wherein the channel is an instrument channel in the endoscope.

18. The method according to claim 13, wherein the endoscope is an ureteroscope.

19. The method according to claim 13, wherein the positioning of the endoscope and the housing at the narrowed region of the lumen in the living body includes positioning the endoscope and the housing at a renal pelvis, at a renal calix or at an entrance to the renal calix, and wherein both the introducing of the liquid into the channel in the endoscope and the rotating of the impeller in the interior of the housing is performed to maintain an average internal pressure at the narrowed region of the lumen in the living body to not exceed 50 cmH$_2$O during the expansion of the narrowed region of the lumen in the living body.

20. A method comprising:
introducing a housing into a living body, the housing possessing an interior with a rotatable impeller positioned in the interior of the housing, the impeller including an inlet and an outlet;
moving the housing in a lumen in the living body;
positioning the housing at a narrowed region of the lumen in the living body; and
rotating the impeller in the interior of the housing while the housing is located in the narrowed region of the lumen in the living body to draw fluid into the inlet and to expel the fluid out of the outlet so that the fluid which is expelled out of the outlet expands the narrowed region of the lumen in the living body to increase an interior size of the narrowed region to an expanded interior size.

* * * * *